United States Patent [19]

Oi et al.

[11] Patent Number: 5,565,069
[45] Date of Patent: Oct. 15, 1996

[54] PROCESS FOR PRODUCING 5-VINYL-2-NORBORNENE

[75] Inventors: Nobuo Oi, Chiba; Kazuo Kimura, Ichihara; Kenichi Nariyama, Sodegaura, all of Japan

[73] Assignee: Sumitomo Chemical Company Limited, Osaka, Japan

[21] Appl. No.: 452,279

[22] Filed: May 26, 1995

[30] Foreign Application Priority Data

May 30, 1994 [JP] Japan .................................. 6-116323

[51] Int. Cl.⁶ ................. B01D 3/34; C07C 2/50
[52] U.S. Cl. .................. 203/30; 203/38; 203/78; 203/80; 585/361; 585/366
[58] Field of Search ................. 203/30, 78, 82, 203/84, 38, 80; 585/361, 366; 202/174; 159/901

[56] References Cited

U.S. PATENT DOCUMENTS

| | | | |
|---|---|---|---|
| 3,590,089 | 6/1971 | Robota | 585/361 |
| 4,205,192 | 5/1980 | Harada | 585/363 |
| 4,777,309 | 10/1988 | Kimura et al. | 585/361 |
| 5,321,177 | 6/1994 | Nakamura et al. | 585/318 |
| 5,378,783 | 1/1995 | Okumura et al. | 526/283 |

FOREIGN PATENT DOCUMENTS

| | | |
|---|---|---|
| 2425290 | 4/1975 | Germany . |
| 4-14648 | 3/1992 | Japan . |
| 4-30381 | 5/1992 | Japan . |
| 5-271113 | 10/1993 | Japan . |

*Primary Examiner*—Nina Bhat
*Attorney, Agent, or Firm*—Sughrue, Mion, Zinn, Macpeak & Seas

[57] ABSTRACT

A process for producing 5-vinyl-2-norbornene which comprises the steps of subjecting a liquid raw material in which tetrahydroindene/dicyclopentadiene ratio (by weight) falls within the range of from 5/100 to 80/100 to a thermal decomposition in liquid phase in the presence of an aromatic hydrocarbon solvent having a boiling point of from 250° C. to 300° C. at a reaction temperature of not lower than 200° C. and lower than 240° C. for a reaction time of from 10 minutes to 120 minutes to obtain a liquid reaction mixture (A-1) composed of 50% to 70% by weight of cyclopentadiene, distilling the liquid reaction mixture (A-1) to obtain fraction (B-1) composed of 90% to 100% by weight of cyclopentadiene and fraction (B-2) composed of 60% to 90% by weight of the total of dicyclopentadiene and tetrahydroindene, further distilling the fraction (B-2) to obtain fraction (B-3) composed of 15% to 40% by weight of dicyclopentadiene and fraction (B-4) composed of 60% to 100% by weight of tetrahydroindene, recycling the fraction (B-3) into the liquid raw material, removing the fraction (B-4) out of the system, and subjecting the fraction (B-1) to a Diels Alder reaction with butadiene to obtain a liquid reaction mixture (C-1) composed of 20% to 40% by weight of 5-vinyl-2-norbornene.

3 Claims, No Drawings

PROCESS FOR PRODUCING 5-VINYL-2-NORBORNENE

The present invention relates to a process for producing 5-vinyl-2-norbornene.

The method for obtaining cyclopentadiene by thermally decomposing dicyclopentadiene in liquid phase is well known. This known method, however, is disadvantageous in that the formation of heavy substances such as cyclopentadiene polymer and the like causes clogging of apparatus and reduces the yield of cyclopentadiene and that, when the starting dicyclopentadiene contains impurities, a large quantity of by-products are formed.

As a means for preventing the clogging of apparatus and reduction of cyclopentadiene yield caused by the formation of heavy substances, it is usual to use an aromatic or paraffinic hydrocarbon solvent having a high boiling point. For example, Japanese Patent Publication KOKOKU No. (JP-B-) 4-30381 discloses a method of carrying out the liquid phase thermal decomposition at a temperature of 240°–280° C. in spindle oil as a solvent.

On the other hand, as a means for preventing the formation of by-products at the time of using dicyclopentadiene containing impurities as raw material, Japanese Patent Publication KOKOKU No. 4-14648 discloses a method of obtaining a high-purity cyclopentadiene by using an aromatic hydrocarbon solvent which suppresses the formation of isoprene.

Further, a method of producing 5-vinyl-2-norbornene from cyclopentadiene and butadiene by Diels Alder reaction is also known. The known method, however, is disadvantageous in that vinylcyclohexene, dicyclopentadiene, tetrahydroindene and polymers thereof are formed as by-products in addition to the intended (objective) vinylnorbornene. Japanese Patent Application KOKAI No. (JP-A-) 61-200930 and Japanese Patent Application KOKAI No. 5-271113 disclose methods for suppressing the formation of by-products by adding a variety of polymerization inhibitors to the reaction system.

If it is intended to obtain 5-vinyl-2-norbornene by combination of these known methods, namely by first thermally decomposing dicyclopentadiene in liquid phase to obtain cyclopentadiene and subsequently subjecting the cyclopentadiene to a Diels Alder reaction with butadiene to obtain 5-vinyl-2-norbornene, and when it is intended to recover and recycle dicyclopentadiene from the reaction mixture containing 5-vinyl-2-norbornene by a conventional separating means in order to minimize the loss of dicyclopentadiene, the fraction of dicyclopentadiene having a boiling point of 163° C. contains a considerable quantity of tetrahydroindene having a boiling point of 160° C. which is relatively close to the boiling point of dicyclopentadiene, and the concentration of the contaminative tetrahydroindene increases after repeated recycling, which reacts partially with cyclopentadiene to lower the yield of cyclopentadiene and decrease the yield of the objective 5-vinyl-2-norbornene.

With the aim of preventing the decrease in the yield of cyclopentadiene and thereby obtaining 5-vinyl-2-norbornene with a high efficiency, the present inventors conducted extensive studies. As a result, it was found that, by distilling the liquid reaction mixture obtained by thermal decomposition of dicyclopentadiene in the first step to separate the mixture into a fraction containing cyclopentadiene, a fraction containing dicyclopentadiene and tetrahydroindene and further distilling the fraction containing dicyclopentadiene and tetrahydroindene to remove the tetrahydroindene out of the system, the reaction between a part of tetrahydroindene and cyclopentadiene can be prevented and the decrease in the yield of cyclopentadiene can be suppressed. Further, it was also found that, since this process involves a step of removing tetrahydroindene out of the system, a starting material containing tetrahydroindene at a high concentration can be used, therefore, 5-vinyl-2-norbornene can be effectively produced. Based on these findings, the present invention was accomplished.

Thus, the present invention provides a process for producing 5-vinyl-2-norbornene which comprises the steps of:

subjecting a liquid raw material in which tetrahydroindene/dicyclopentadiene ratio (by weight) falls within the range of from 5/100 to 80/100 to a thermal decomposition in liquid phase in the presence of an aromatic hydrocarbon solvent having a boiling point of from 250° to 300° C. at a reaction temperature of not lower than 200° C. and lower than 240° C. for a reaction time of from 10 minutes to 120 minutes to obtain a liquid reaction mixture (A-1) composed of 50% to 70% by weight of cyclopentadiene, distilling the liquid reaction mixture (A-1) to obtain fraction (B-1) composed of 90% to 100% by weight of cyclopentadiene and fraction (B-2) composed of 60% to 90% by weight of the total of dicyclopentadiene and tetrahydroindene, further distilling the fraction (B-2) to obtain fraction (B-3) composed of 15% to 40% by weight of dicyclopentadiene and fraction (B-4) composed of 60% to 100% by weight of tetrahydroindene, recycling the fraction (B-3) into the liquid starting (raw) material, removing the fraction (B-4) out of the system, and subjecting the fraction (B-1) to a Diels Alder reaction with butadiene to obtain a liquid reaction mixture (C-1) composed of 20% to 40% by weight of 5-vinyl-2-norbornene.

In the present invention, the thermal decomposition in liquid phase is carried out in the presence of an aromatic hydrocarbon solvent having a boiling point of 250°–300° C., at a temperature of 200°–240° C. for a reaction time of 10–120 minutes, under a condition that the liquid starting material to be subjected to the thermal decomposition has a tetrahydroindene/dicyclopentadiene ratio (by weight) of from 5/100 to 80/100.

In the liquid starting material to be subjected to the thermal decomposition in liquid phase, the ratio (by weight) tetrahydroindene/dicyclopentadiene must be in the range of from 5/100 to 80/100. If the ratio is greater than 80/100, the side reaction between tetrahydroindene and cyclopentadiene (objective compound) remarkably takes places in the course of the thermal decomposition to lower the yield of cyclopentadiene. If the ratio is smaller than 5/100, prior processes are sufficient.

In the thermal decomposition in liquid phase, an aromatic hydrocarbon solvent having a boiling point of 250°–300° C. is used. If a solvent having a boiling point of lower than 250° C. is used, evaporation of such a solvent requires a large quantity of thermal energy. On the other hand, a solvent having a boiling point exceeding 300° C. generally has a high viscosity which results to disadvantageous from the viewpoint of reaction yield and workability.

The aromatic hydrocarbon solvent must be stable thermally and chemically and inert to cyclopentadiene and dicyclopentadiene under the conditions of the thermal decomposition in liquid phase. Examples of such solvent include diphenyl, diphenylmethane, diphenylethane, diphenyl ether, and the alkylbenzenes which are obtained as still residue in the processes for producing ethylbenzene, cumene, cymene, mixtures thereof, etc. As such alkylbenzene, those containing the components having a boiling point range of 250°–300° C. in an amount of at least 70% by volume, and preferably at least 80% by volume, are preferred. Since such alkylbenzenes usually has only fuel use, the use of such alkylbenzenes as a solvent can bring about a great improvement in economy of the process.

The solvent is used usually in an amount of from 5 to 80% by weight, preferably in an amount of from 15 to 75% by weight, based on the sum of the starting material and solvent. If proportion of the solvent is too high, the discharge from decomposition reactor into outer system increases which is accompanied by losses of cyclopentadiene and dicyclopentadiene. On the other hand, if proportion of the solvent is too low, the liquid material in the decomposition reactor is inferior in fluidity, which can make a trouble on the workability of continuous operation.

The aromatic hydrocarbon used in the present invention presumably has an action of accelerating the thermal decomposition and an action of suppressing the formation of heavy substances, so that in its presence the decomposition reaction progresses at a temperature lower than the conventional thermal decomposition temperatures. These actions are exhibited particularly explicitly when a dicyclopentadiene containing tetrahydroindene as an impurity is used as starting material.

The reaction temperature of the thermal decomposition in liquid phase falls within the range of 200°–240° C. and preferably 210°–240° C. If the reaction temperature is lower than 200° C., decomposition rate of dicyclopentadiene decreases, which brings about a decrease in cyclopentadiene yield. On the other hand, if the reaction temperature is higher than 240° C., vaporization of the solvent used for the reaction is promoted, which requires to supply a large quantity of thermal energy to the reaction system. Further, a step of cooling must be provided before shifting to the subsequent step of distillation, which requires a very large-sized condenser and deteriorates economy of the process.

It is recommendable to use a forced circulation type heat exchanger as a heating means for maintaining the reaction temperature.

The pressure at the time of decomposition reaction is not particularly limited, but any pressure may be adopted so that the reaction temperature can be adjusted so as to fall within the above-specified range under the adopted pressure. Usually, a pressure of from 0.5 atmosphere to 5 atmospheres is adopted.

The reaction time of the thermal decomposition in liquid phase falls within the range of 10–120 minutes, and preferably 10–60 minutes. If the reaction time is shorter than 10 minutes, decomposition rate of dicyclopentadiene is low. On the other hand, if the reaction time is longer than 120 minutes, a side reaction between tetrahydroindene and cyclopentadiene in the starting material progresses, which brings about a reduction in the yield of cyclopentadiene.

The method for feeding the starting dicyclopentadiene is not particularly limited. That is, the starting dicyclopentadiene may be mixed with a solvent before feeding it to decomposition reactor, or may be fed to the decomposition reactor in itself alone.

If desired, the starting material to be fed to the decomposition reactor may be pre-heated to a temperature not exceeding the boiling point of dicyclopentadiene.

In order to prevent accumulation of the high-boiling components such as cyclopentadiene polymer and the like formed as by-products in the decomposition reactor and the high-boiling components originally including in the starting material, it is possible, if desired, to discharge the liquid material including in the decomposition reactor directly and partially, either continuously or intermittently, or to transfer the liquid material including in the decomposition reactor to the subsequent fractionating column where the useful components such as cyclopentadiene and dicyclopentadiene are recovered and then a part of the still residue is discharged out of the system. In these cases, the still residue which has been discharged out of the system can be returned to the decomposition reactor together with starting material. It is preferable to supply a quantity of fresh solvent in accordance with the quantity of discharge from the system in order to keep the constant quantity of liquid material in the decomposition reactor.

The decomposition reaction in liquid phase can be practiced with, for example, an apparatus provided with a decomposition reactor, a heater, a fractionating column, a condenser and a cooler.

The mixture of dicyclopentadiene and solvent which has been fed to the decomposition reactor may be heated to a prescribed temperature by means of a forced circulation type heat exchanger, or may be recycled after a partial discharge out of the system in order to keep the constant quantity of liquid material remaining in the decomposition reactor.

A liquid reaction mixture (A-1) composed of 50% to 70% by weight of cyclopentadiene is obtained by liquid phase thermal decomposition of the liquid starting material. The liquid reaction mixture (A-1) is subjected to a distillation to give fraction (B-1) composed of 90 to 100% by weight of cyclopentadiene and fraction (B-2) composed of 60% to 90% by weight of the total of dicyclopentadiene and tetrahydroindene.

The distillation for obtaining the fraction (B-1) composed of 90% to 100% by weight of cyclopentadiene and the fraction (B-2) composed of 60% to 90% by weight of the total of dicyclopentadiene and tetrahydroindene from reaction mixture (A-1) (hereinafter, this distillation is referred to as "distillation ($b_1$)") is carried out at a column top temperature of 10°–50° C., a column top pressure of 0.2–1.5 atmosphere and a reflux ratio of 0.1–3.

The fraction (B-2) composed of 60% to 90% by weight of the total of dicyclopentadiene and tetrahydroindene which has been obtained through the distillation ($b_1$) is further subjected to a distillation (hereinafter, this distillation is referred to as "distillation ($b_2$)"), by which fraction (B-3) composed of 15% to 40% by weight of dicyclopentadiene and fraction (B-4) composed of 60% to 100% by weight of tetrahydroindene are obtained. The distillation ($b_2$) is carried out at a column top temperature of 20°–100° C., a column top pressure of 0.05–0.8 atmosphere, and a reflux ratio of 10–40.

Among the fractions obtained through distillation ($b_2$), the fraction (B-3) is recycled into the starting liquid material, while the fraction (B-4) containing tetrahydroindene is purged out of the system. It is necessary to control the quantity of tetrahydroindene to be purged out of the system so that the tetrahydroindene/dicyclopentadiene ratio (by weight) in the liquid starting material falls within the range of from 5/100 to 80/100.

The concentration of tetrahydroindene in the fraction (B-2) may vary with the reaction conditions and process conditions. A higher concentration of tetrahydroindene in fraction (B-2) is generally preferable from the viewpoint of minimizing the loss of dicyclopentadiene. Usually, the concentration is 5% by weight or more, preferably 20% by weight or more, and more preferably 30% by weight or more, and most preferably 40% by weight or more.

The fraction (B-1) composed of 90% to 100% by weight of cyclopentadiene, obtained through the distillation $(b_1)$, is subjected to a Diels Alder reaction with butadiene to form liquid reaction mixture (C-1) composed of 20% to 40% by weight of 5-vinyl-2-norbornene.

Reaction temperature of the Diels Alder reaction usually falls within the range of 80°–180° C., and preferably 90°–150° C. If the reaction temperature is lower than 80° C., the conversion and the product yield may decrease. On the other hand, if the reaction temperature is higher than 180° C., formation of various by-products such as polymers, tetrahydroindene and the like increases, and the selectivity toward the objective 5-vinyl-2-norbornene may decrease.

Pressure of the reaction is not particularly limited, and it is usually from about 10 atmosphere to about 50 atmosphere.

The reaction time usually falls within the range of from 0.1 hour to 5 hours, and preferably from 0.3 hour to 2 hours. If the reaction time is too short, product yield may decrease. If the reaction time is too long, selectivity toward the objective product may decrease.

The molar ratio butadiene/cyclopentadiene adopted in the reaction usually falls within the range of from 0.2/1 to 10/1, and preferably from 0.5/1 to 3/1. If the ratio is out of the above-specified range, product yield and selectivity toward the objective product may decrease and the quantity of recycled unreacted component may increase. The lower conversion in the Diels Alder reaction, the higher selectivity toward the objective product. Therefore, a distillation column is established just after the Diels Alder reactor to separate and recover unreacted butadiene and cyclopentadiene from the column top for recycling them into the Diels Alder reactor.

The reaction can be carried out in a pressure-resistant vessel, in the presence or absence of additives such as solvent, catalyst, polymerization inhibitor and the like, by the batch method or continuous method.

The reaction mixture (C-1) thus obtained contains dicyclopentadiene as a by-product and tetrahydroindene as an impurity in addition to 5-vinyl-2-norbornene as the objective product.

If desired, the liquid reaction mixture (C-1) may be subjected to a distillation (hereinafter, this distillation is referred to as "distillation $(d_1)$"). After separating the mixture (C-1) into fraction (D-1) composed of 95% to 100% by weight of 5-vinyl-2-norbornene and fraction (D-2) composed of 70% to 100% by weight of dicyclopentadiene, the fraction (D-2) may be recycled into the liquid starting material, if desired.

The distillation $(d_1)$ is carried out at a column top temperature of 40°–150° C. at a column top pressure of 0.05–1.2 atmosphere.

The fraction (D-2) composed of 70% to 100% by weight of dicyclopentadiene is preferably recycled into the liquid starting material. The content of tetrahydroindene in the fraction (D-2) is usually as low as about 0.01% to about 10% by weight. Accordingly, a procedure of additionally distilling the fraction (D-2) and thereby separating tetrahydroindene therefrom consumes a large quantity of energy and, therefore is uneconomical.

When the liquid reaction mixture (C-1) contains impurities of which boiling point is lower than that of 5-vinyl-2-norbornene, a distillation for removing such impurities can be practiced as a pre-stage of the distillation $(d_1)$.

EXAMPLES

Next, the present invention is further explained by referring to the following non-limitative examples.

Examples 1–3 and Comparative Examples 1–2

A decomposition reactor is continuously fed with a liquid mixture of starting dicyclopentadiene and a solvent containing a varied quantity of tetrahydroindene. The decomposition reactor was previously charged with 100 g of solvent. At an ordinary pressure, the reaction temperature and the reaction time are varied, and the gaseous reaction product is recovered from the decomposition reactor. A part of the liquid phase is discharged from the decomposition reactor in order to keep the constant quantity of liquid material in the decomposition reactor. The results of the reaction are summarized in Tables 1 and 2.

It is understandable that the recovery rate of cyclopentadiene and dicyclopentadiene can be maintained at 92% or above and the recovery rate of cyclopentadiene can be maintained at 72% or above by controlling the tetrahydroindene/dicyclopentadiene ratio (by weight) in the liquid material to be fed into the thermal decomposition step so as to fall within the range of from 5/100 to 80/100.

TABLE 1

|  | Example | | |
| --- | --- | --- | --- |
|  | 1 | 2 | 3 |
| Conditions |  |  |  |
| THI concentration *1 | 5 | 30 | 70 |
| Solvent *2 | DPE | DPE | DPE |
| Mixing ratio *3 | 2/1 | 2/1 | 2/1 |
| Reaction temperature (°C.) | 230 | 230 | 230 |
| Reaction time (min.) *4 | 23 | 29 | 27 |
| Results |  |  |  |
| Recovery rate of CPE + DCPD (%) *5 | 95.3 | 94.2 | 93.0 |
| Recovery rate of CPD (%) *6 | 80.0 | 77.1 | 73.0 |

TABLE 2

|  | Comparative Example | |
| --- | --- | --- |
|  | 1 | 2 |
| Conditions |  |  |
| THI concentration *1 | 52 | 95 |
| Solvent *2 | DPE | DPE |
| Mixing ratio *3 | 2/1 | 2/1 |
| Reaction temperature (°C.) | 190 | 230 |
| Reaction time (min.) *4 | 26 | 23 |
| Results |  |  |
| Recovery rate of CPD + DCPD (%) *5 | 55.7 | 90.8 |
| Recovery rate of CPD (%) *6 | 44.8 | 69.2 |

*1 THI concentration: the quantity of tetrahydroindene (parts by weight) per 100 parts by weight of dicyclopentadiene in the liquid starting material.
*2 Solvent: DPE: Diphenyl ether (bp 259° C.)
*3 Mixing ratio: the ratio (by weight) of solvent to starting dicyclopentadiene containing tetrahydroindene fed to reactor; (weight of solvent)/(weight of starting dicyclopentadiene)
*4 Reaction time: determined from (quantity of liquid material in the decomposition reactor)/(withdrawing rate of liquid phase from decomposition reactor)
*5 Recoverty rate of CPD + DCPD; [(total weight of CPD and DCPD in the gaseous reaction product)/(weight of fed DCPD)] × 100%
*6 Recovery rate of CPD: [(weight of CPD in the gaseous reaction product)/(weight of fed DCPD)] × 100%
wherein CPD represents cyclopentadiene and DCPD represents dicyclopentadiene.

Example 4

A reaction is carried out with a system consisting of one decomposition reactor, one Diels Alder reactor and three distillation columns. A mixture of a starting dicyclopentadiene material containing tetrahydroindene and a solvent (weight ratio of 2:5) is continuously fed to the decomposition reactor, and a reaction is carried out at ordinary pressure, at 230° C., for a reaction time of 40 minutes, wherein the reaction time expresses a ratio of (quantity of liquid material in the decomposition reactor)/(withdrawing rate of liquid phase from the decomposition reactor). The ratio of tetrahydroindene/dicyclopentadiene (by weight) in the liquid starting material is adjusted to 5/100. The decomposition reactor is previously charged with 300 liters of PAB as a solvent. (PAB: the still residue in the ethylbenzene production process; a mixture of aromatic hydrocarbons such as triethylbenzene, diphenylethane and the like; initial boiling point 252° C., 85% by weight distills out in the temperature range up to 300° C.) A part of the liquid phase in the decomposition reactor is continuously discharged out of the system so as to keep the constant quantity of liquid in the decomposition reactor. The gaseous reaction product formed in the decomposition reactor is recovered, fed to the first distillation column, and rectified at a column top pressure of 1.0 atmosphere, a column bottom pressure of 1.1 atmosphere, and a reflux ratio of 0.4. Fraction (B-1) composed mainly of cyclopentadiene is obtained from the column top, and fraction (B-2) composed mainly of dicyclopentadiene and tetrahydroindene is obtained from the column bottom. The fraction (B-2) is sent to the second distillation column, and rectified at a column top pressure of 0.13 atmosphere, a column bottom pressure of 0.16 atmosphere and a reflux ratio of 27. Fraction (B-4) composed mainly of tetrahydroindene is obtained from the column top, and fraction (B-3) composed mainly of dicyclopentadiene is obtained from the column bottom. The fraction (B-3) is recycled into the decomposition reactor, while the fraction (B-4) is discharged out of the system. As a result, the recovery rate of cyclopentadiene (the quantity of cyclopentadiene (parts by weight) in the fraction (B-1) per 100 parts by weight of dicyclopentadiene in the liquid starting material) is 83.5%, and the recovery rate of cyclopentadiene and dicyclopentadiene (total quantity (parts by weight) of cyclopentadiene and dicyclopentadiene in the fraction (B-1) per 100 parts by weight of dicyclopentadiene in the liquid starting material) is 84.5%.

The fraction (B-1) and the starting butadiene material are fed to the Diels Alder reactor and the Diels Alder reaction is carried out at a temperature of 135° C. and a pressure of 23 atmosphere. The molar ratio of butadiene/cyclopentadiene in the liquid to be subjected to the Diels Alder reaction is 1.5/1. The liquid reaction mixture obtained is fed to the third distillation column, and rectified at a column top pressure of 1.3 atmosphere, a column bottom pressure of 1.4 atmosphere, and a reflux ratio of 0.33. Butadiene and cyclopentadiene are recovered from the column top, and recycled to the Diels Alder reactor to obtain fraction (C-1) containing 5-vinyl-2-norbornene, dicyclopentadiene and tetrahydroindene from the column bottom.

As a result, conversion of 5-vinyl-2-norbornene (the molecular number of 5-vinyl-2-norbornene in the fraction (C-1) per 50 moles of dicyclopentadiene in the liquid starting material) is 20.0%.

Comparative Example 3

A reaction is carried out with a system consisting of one decomposition reactor, one Diels Alder reactor and two distillation columns. A mixture of a starting dicyclopentadiene material containing tetrahydroindene and a solvent (weight ratio of 2:5) is continuously fed to the decomposition reactor, and a reaction is carried out at the same temperature, pressure, reaction time and quantity of charged solvent as in Example 4. The ratio of tetrahydroindene/dicyclopentadiene (by weight) in the liquid starting material is adjusted to 5/100. A part of the liquid phase in the decomposition reactor is continuously discharged out of the system so as to keep constant the quantity of liquid in the decomposition reactor. The gaseous reaction product formed in the decomposition reactor is recovered, fed to the first distillation column, and rectified at the same column top pressure, column bottom pressure and reflux ratio as in Example 4. Fraction (B-1) composed mainly of cyclopentadiene is obtained from the column top, and fraction (B-2) composed mainly of dicyclopentadiene and tetrahydroindene is obtained from the column bottom. The fraction (B-2) is discharged out of the system. As a result, the recovery rate of cyclopentadiene (the quantity of cyclopentadiene (parts by weight) in the fraction (B-1) per 100 parts by weight of dicyclopentadiene in the liquid starting material) is 74.0%, and the recovery rate of cyclopentadiene and dicyclopentadiene (total quantity (parts by weight) of cyclopentadiene and dicyclopentadiene in the fraction (B-1) per 100 parts by weight of dicyclopentadiene in the liquid starting material) is 75.0%.

The fraction (B-1) and the starting butadiene material are fed to the Diels Alder reactor and the Diels Alder reaction is carried out at the same temperature, pressure, and molar ratio of butadiene/cyclopentadiene as in Example 4. The liquid reaction mixture obtained is fed to the distillation column, and rectified at the same column top pressure, column bottom pressure, and reflux ratio as the third distillation column in Example 4. Butadiene and cyclopentadiene are recovered from the column top, and recycled to the Diels Alder reactor to obtain fraction (C-1) containing 5-vinyl-2-norbornene, dicyclopentadiene and tetrahydroindene.

Conversion of 5-vinyl-2-norbornene (the molecular number of 5-vinyl-2-norbornene in the fraction (C-1) per 50 moles of dicyclopentadiene in the liquid starting material) is 12.0%.

Example 5

A reaction is carried out with a system consisting of one decomposition reactor, one Diels Alder reactor and five distillation columns. A mixture of a starting dicyclopentadiene material containing tetrahydroindene and a solvent (weight ratio of 2:5) is continuously fed to the decomposition reactor, and a reaction is carried out at the same temperature, pressure, reaction time and quantity of charged solvent as in Example 4. The ratio of tetrahydroindene/dicyclopentadiene (by weight) in the liquid starting material is adjusted to 5/100. A part of the liquid phase in the decomposition reactor is continuously discharged out of the system so as to keep the constant quantity of liquid in the decomposition reactor. The gaseous reaction product formed in the decomposition reactor is recovered, fed to the first distillation column (distillation "$b_1$"), and rectified at the same column top pressure, column bottom pressure, and reflux ratio as in Example 4. Fraction (B-1) composed mainly of cyclopentadiene is obtained from the column top, and fraction (B-2) composed mainly of dicyclopentadiene and tetrahydroindene is obtained from the column bottom. The fraction (B-2) is sent to the second distillation column (distillatior "$b_2$"), and rectified at the same column top pressure, column bottom pressure and reflux ratio as in Example 4. Fraction (B-4) composed mainly of tetrahydroindene is obtained from the column top, and fraction (B-3) composed mainly of dicyclopentadiene is obtained from the column bottom. The fraction (B-3) is recycled into the decomposition reactor, while the fraction (B-4) is discharged out of the system.

The fraction (B-1) and the starting butadiene material are fed to the Diels Alder reactor and the Diels Alder reaction is carried out at the same temperature, pressure, and molar ratio of butadiene/cyclopentadiene as in Example 4. A liquid reaction mixture obtained is fed to the third distillation column, and rectified at the same column top pressure, column bottom pressure, and reflux ratio as in Example 4. Butadiene and cyclopentadiene are recovered from the column top, and recycled to the Diels Alder reactor to obtain fraction (C-1) containing 5-vinyl-2-norbornene, dicyclopentadiene and tetrahydroindene.

The fraction (C-1) is fed to the fourth distillation column, and rectified at a column top pressure of 0.08 atmosphere, a column bottom pressure of 0.09 atmosphere, and a reflux ratio of 30. A fraction containing components having a boiling point lower than that of 5-vinyl-2-norbornene is obtained from the column top, and a fraction containing 5-vinyl-2-norbornene, dicyclopentadiene and tetrahydroindene is obtained from the column bottom. Further, the fraction from the column bottom is fed to the fifth distillation column (distillation "$d_1$"), and rectified at a column top pressure of 0.03 atmosphere, a column bottom pressure of 0.06 atmosphere, and a reflux ratio of 4.6. Component (D-1) composed mainly of 5-vinyl-2-norbornene is obtained from the column top, and component (D-2) composed mainly of dicyclopentadiene is obtained from the column bottom. The fraction (D-2) is recycled to the decomposition reactor.

As a result, conversion of 5-vinyl-2-norbornene (the molecular number of 5-vinyl-2-norbornene in the fraction (C-1) per 50 moles of dicyclopentadiene in the liquid starting material) is 50.0%.

What is claimed is:

1. A process for producing 5-vinyl-2-norbornene which comprises the steps of:

subjecting a liquid raw material in which tetrahydroindene/dicyclopentadiene ratio by weight falls within the range of from 5/100 to 80/100 to a thermal decomposition in liquid phase in the presence of an aromatic hydrocarbon solvent having a boiling point of from 250° C. to 300° C. at a reaction temperature of not lower than 200° C. and lower than 240° C. for a reaction time of from 10 minutes to 120 minutes to obtain a liquid reaction mixture (A-1) composed of 50% to 70% by weight of cyclopentadiene, distilling the liquid reaction mixture (A-1) to obtain fraction (B-1) composed of 90% to 100% by weight of cyclopentadiene and fraction (B-2) composed of 60% to 90% by weight of the total of dicyclopentadiene and tetrahydroindene, further distilling the fraction (B-2) to obtain fraction (B-3) composed of 15% to 40% by weight of dicyclopentadiene and fraction (B-4) composed of 60% to 100% by weight of tetrahydroindene, recycling the fraction (B-3) into the liquid raw material, removing the fraction (B-4) out of the system, and subjecting the fraction (B-1) to a Diels Alder reaction with butadiene to obtain a liquid reaction mixture (C-1) composed of 20% to 40% by weight of 5-vinyl-2-norbornene.

2. The process according to claim 1, further including the steps of distilling the liquid reaction mixture (C-1) to obtain fraction (D-1) composed of 95% to 100% by weight of 5-vinyl-2-norbornene and fraction (D-2) composed of 70% to 100% by weight of dicyclopentadiene, and recycling the fraction (D-2) into the liquid raw material.

3. The process according to claim 1, wherein the reaction temperature of the thermal decomposition in liquid phase is not lower than 210° C. and lower than 240° C.

* * * * *